United States Patent [19]

Cohen

[11] 4,023,932

[45] May 17, 1977

[54] REACTOR FOR ANALYSIS OF POLLUTED LIQUIDS

[76] Inventor: Alfred Cohen, 71 Joyce Lane, Woodbury, N.Y. 11797

[22] Filed: Dec. 16, 1974

[21] Appl. No.: 533,247

Related U.S. Application Data

[63] Continuation-in-part of Ser. No. 179,964, Sept. 13, 1971, Pat. No. 3,854,881.

[52] U.S. Cl. .......................... 23/253 PC; 23/277 R; 23/281; 261/94
[51] Int. Cl.² .................... B01J 8/02; G01N 31/12; G01N 33/18
[58] Field of Search ..... 23/253 PC, 230 PC, 230 R, 23/253 R, 284, 277 R, 281, 288 R; 261/94, 95, 96, 97, 98; 55/233

[56] References Cited

UNITED STATES PATENTS

| 2,718,457 | 9/1955 | McKinnis | 23/277 R X |
| 3,025,145 | 3/1962 | Terpenning, Jr. | 23/281 X |
| 3,468,637 | 9/1969 | Hammond | 261/94 X |
| 3,801,288 | 4/1974 | Leas et al. | 23/277 R X |

Primary Examiner—Robert M. Reese
Attorney, Agent, or Firm—Bucknam and Archer

[57] ABSTRACT

A reactor for use in analysis of polluted liquids, having a housing partitioned into an inner flow passage communicated with an inlet, and an outer flow passage surrounding the inner flow passage and flow connected therewith. A packing material is arranged in the inner and outer flow passages to define an inlet plenum zone in the inner passage. Means are provided for heating the packing material to a temperature at which a liquid sample is vaporized in the inlet plenum zone and reacts with a gas while flowing therewith through the inner and outer passage to an outlet of the outer passage.

3 Claims, 3 Drawing Figures

U.S. Patent
May 17, 1977
4,023,932
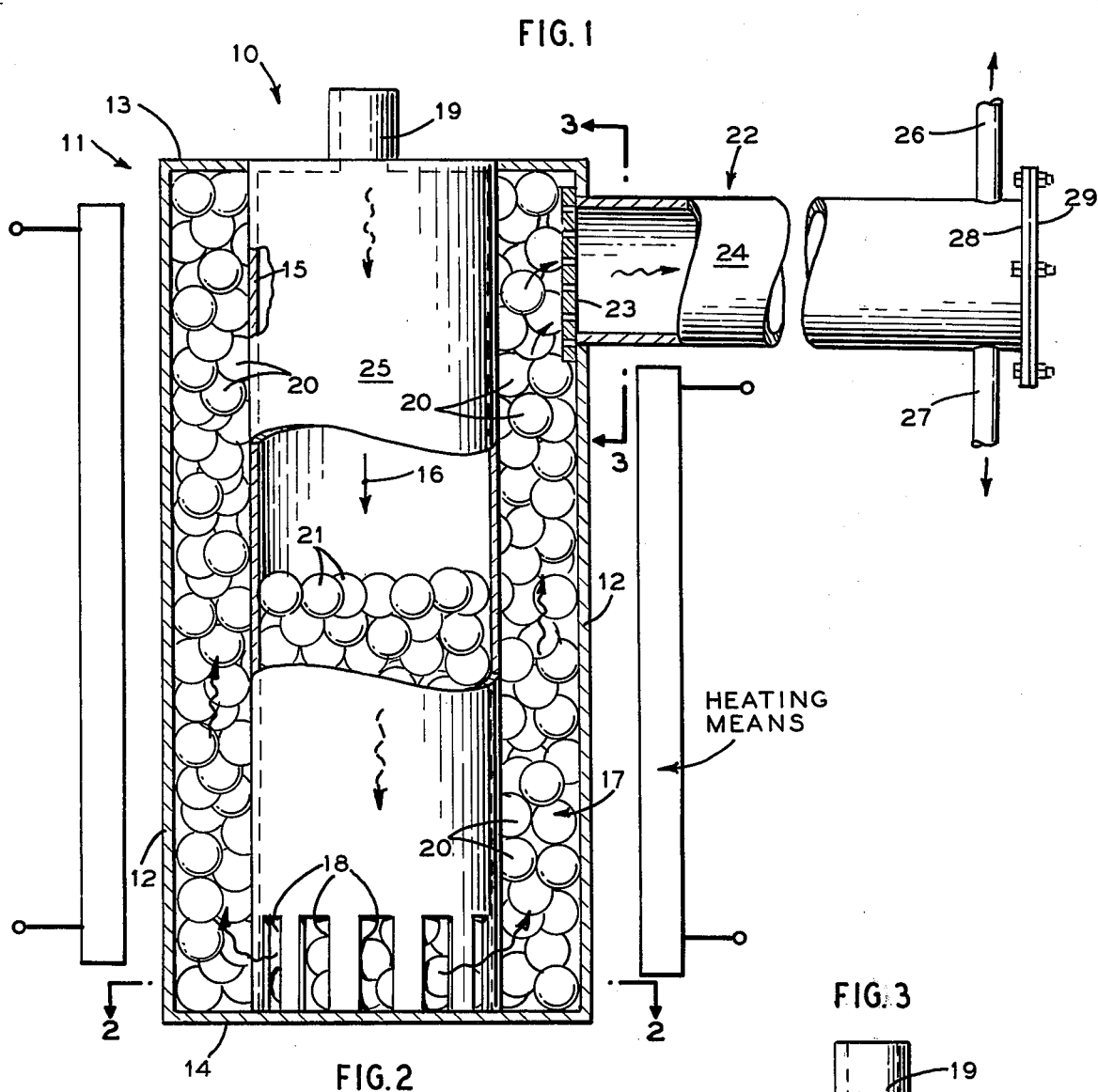
FIG. 1
FIG. 3
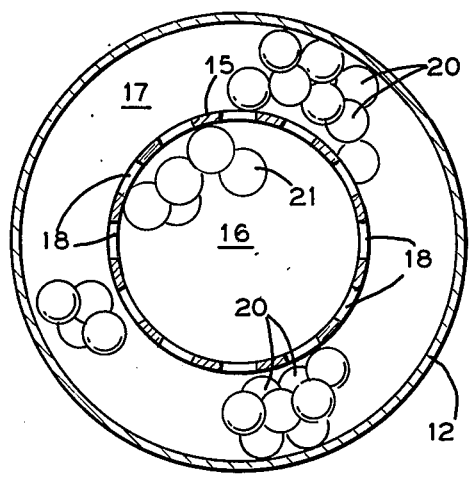
FIG. 2

4,023,932

REACTOR FOR ANALYSIS OF POLLUTED LIQUIDS

This application is a continuation-in-part of my prior patent application Ser. No. 179,964, filed Sept. 13, 1971, now U.S. Pat. No. 3,854,881.

BACKGROUND AND SUMMARY OF THE INVENTION

This invention relates in general to equipment for the analysis of liquids, and more particularly to a reactor for use in the analysis of polluted liquids.

In my prior patent application Ser. No. 179,964, filed Sept. 13, 1971, now U.S. Pat. No. 3,854,881 issued Dec. 17, 1974 there is described an analytical apparatus for determining the total quantity of organic carbon as a pollutant in an aquaeous stream. A sample of liquid is taken from the stream and reacted with acid to remove all of the inorganic carbon, i.e. carbonates, of the sample of formation of carbon dioxide. The acidified sample is scrubbed to remove all carbon dioxide produced by the carbonate-acid reaction, and the carbonate-free sample is introduced by a metering device into a reaction chamber, along with air for oxidizing the organic carbon of the sample to carbon dioxide. The gaseous and vapor reaction products in the effluent from the reaction chamber will therefore include water vapor and carbon dioxide. The water vapor portion of the effluent is ordinarily removed by a condensor or conventional liquid-gas separator, before passage to an infrared analyzer for measurement of the carbon dioxide component.

By the amount of carbon dioxide present in the reactor effluent, the amount of organic carbon originally present in the sample can be determined.

The subject invention is directed to a modified reactor structure that has been found to give somewhat better performance than the reactor configuration shown in my patent application Ser. No. 179,964.

The reactor of this invention comprises a housing, partition means disposed within said housing to define therein an inner flow passage and an outer flow passage disposed in laterally surrounding relation to said inner flow passage and flow connected therewith, means defining an inlet in said housing to accommodate the introduction therein of a liquid sample and a gas to be reacted with said sample, a packing material disposed in said inner flow passage to define therein an inlet plenum zone communicating with said inlet, and a packing material disposed in said outer flow passage, means defining an outlet in said housing communicating with said outer flow passage, and means operable to heat the packing material in said inner and outer flow passages to a temperature at which the sample is vaporized in said inlet plenum zone and the sample reacts with said gas while flowing therewith through said inner and outer passages in contact with the packing material, the gaseous and vapor reaction products of said sample and gas exiting the housing through said outlet.

The housing and partition means are expediently tubular cylindrical shells, arranged in generally coaxial relation between a pair of plates connected to the ends of the larger diameter shell forming therewith an enclosed housing. The inner flow passage is thus cylindrical and is communicated with the annular outer flow passage by slots in the inner shell.

The packing material in used both flow passages is chemically inert and is of a material such as ceramic, glass, quartz and the like. Expediently, the packing material is in the form of relatively small balls which are of a quantity sufficient to occupy approximately the entire volume of the outer flow passage and about one-half the volume of the inner flow passage. These balls are disposed one against the other so as to provide in such flow passages voids accommodating fluid flow therethrough.

The inlet of the reactor is expediently on the upper cover plate, such that the sample and reagent gas, usually air, introduced through the inlet enters the inlet plenum zone defined by the open space above the packing in the inner flow passage, the liquid components of the sample are vaporized before contacting the packing, and then vapor and gas mixture flows downward through the inner passage, radially outward into the outer passage, and upward therethrough.

On the outer wall of the housing is provided an outlet communicating with a second housing which constitutes an outlet plenum chamber. The reaction products of the sample and air or other reagent gas exit through this outlet and are received in such plenum chamber where they undergo cooling before passing to subsequent apparatus and instruments.

As compared with the reactor described in U.S. Pat. No. 3,854,881, the reactor designed which is the subject of this application provides a packing material that is arranged in laterally surrounding relation to the inlet plenum zone and thereby provides a laterally inward heat flux to such plenum zone over the axial length thereof, and just at one end of the plenum zone as was the case in the aforesaid earlier reactor. This gives a more uniform temperature description within the inlet plenum zone and assures complete vaporization of any liquid sample before it contacts the packing material in the inner flow passage. In addition, the reaction products exit the reactor described herein through an outlet in the outer wall and pass through a second housing defining an outlet plenum chamber extending laterally away from the first housing containing the inner and outer flow passages. This second housing provides for cooling the reaction products and for separate drainage for such products as are condensed to liquid.

For a better understanding of the invention and its various advantages, reference should be had to the following detailed description and accompanying drawings which together exemplify a preferred embodiment of the invention.

BRIEF DESCRIPTION OF THE DRAWINGS

In the drawings:

FIG. 1 is an elevation view, partly in section, of a reactor according to a preferred embodiment of the invention.

FIG. 2 is a sectional view of the reactor shown in FIG. 1 as taken along line 2—2 therein, and showing the general arrangement of the tube walls that define the inner and outer flow passages of the reactor.

FIG. 3 is a sectional view of the reactor shown in FIG. 1 as taken along line 3—3 therein, and showing details of the outlet plenum zone of the reactor.

DESCRIPTION OF A PREFERRED EMBODIMENT OF THE INVENTION

In FIGS. 1–3 there is explified a reactor 10 according to a preferred embodiment of the invention. Reactor 10 expediently comprises a housing 11 formed by an outer cylindrical shell 12 closed at both ends by respective plates 13 and 14.

Within housing 11 is disposed generally coaxial with the shell 12, a tubular cylindrical shell partition 15 joined in gas-tight sealing relation to the upper plate 13 and set in abutting relation to the lower plate 14. Partition 15 defines within housing 11 an inner flow passage 16 and an outer flow passage 17 disposed in laterally surrounding relation to inner passage 16 and flow connected therewith through a series of circumferentially spaced slots 18 in the end of partition 15 adjacent plate 14.

On plate 13 is provided an inlet 19 through which the liquid sample and air, (or other reagent gas), is introduced into an inlet plenum zone 25 of passage 16.

Within the passages 16 and 17 are disposed a packing material in the form of pluralities of respective balls 20 and 21. These balls 20 and 21 are of a relatively small diameter as compared with the diametral difference between shells 15 and 16 and are disposed in contact with one another so as to establish voids accommodating fluid flow through passages 16 and 17. Balls 20 and 21 can be of the same size or of different sizes and are made of a chemically inert material such as a ceramic, glass, quartz or the like.

Balls 20 occupy approximately the entire space of the annular outer passage 17 whereas balls 21 occupy approximately the lower half of the space of the cylindrical inner passage 16. The upper half of the passage 16, above the balls 21 defines the inlet plenum zone 25.

To the upper portion of the outer shell 12 is connected one end of a transversely extending cylindrical tubular shell 22 that can be considered as a second housing which defines an outlet plenum zone 24. Shell 22 communicates with an outlet opening in the outer wall 12 boundary of passage 17. Across the open end of shell 22 is secured a perforated plate 23 which serves to retain the balls 20 within passage 17 but allows gaseous and vapor reaction products to pass into plenum zone 24 where these reaction products are cooled before being passed to a condensor and gas analyzing equipment (not shown).

The opposite end of shell 22 is provided with outlets 26 and 27 for delivering reaction products to such other equipment, and a flange 28 to which a cover plate 29 is secured to seal that end of shell 22.

Upwardly directed outlet 26 is commonly connected to a condensor or gas-liquid separator (not shown) and downwardly directed outlet 27 is expediently used to drain any condensed liquid from plenum zone 24. To facilitate drainage the shell 22 is arranged with its axis slanted downward at about 3 to 5 degrees from the horizontal, the axis of housing shell 12 being normally in a generally vertical orientation.

In operation of reactor 10, the packing balls 20 and 21, (as well as the shells 12, 15 and plate 13, 14) are heated to a relatively high temperature at which the organic carbon in the sample liquid is oxidized to carbon dioxide by air. For such purpose are provided heating means, expediently composed of a plurality of electric heater elements disposed in surrounding spaced relation to the shell 12.

The sample liquid introduced along with the reagent air through inlet 19 is vaporized in the plenum zone 24, the temperature of which is kept high enough so that no cold liquid impinges upon the packing balls 21. What flows through the packed lower portion of passage 16 is a mixture of water vapor, suspended carbonaceous solids and air reacting with such solids as the flow progresses.

The reacting mixture flows downward through passage 16 and through slots 18 radially outward into passage 17 and thence upwardly therein to plenum zone 24 through the perforations of plate 23.

The advantage offered by the illustrated reactor 10 configuration is that a more uniform and effective heating of plenum zone 25 can be obtained because of the hot packing balls 20 in the surrounding outer passage 17. Thus, in addition to the axial heat flow into plenum zone 25 from the balls 21 in passage 16, there is a radially inward heat flow from the outer passage balls 20.

While the dimensions of the various parts of the reactor 10 can be varied somewhat, a satisfactory reactor 10 performance has been achieved where the height or length of the shell 12 is about twice its diameter, and the radial difference between the shells 12 and 15 is about one-fourth to one third the radius of outer shell 12. The plenum zone 24 is suitably about one-third the diameter of shell 12 and about two-thirds the length thereof.

From the foregoing description it will become apparent to the artisan that the invention is adaptable to many specific applications, and that obvious changes can be made in the illustrated apparatus to suit the needs of particular installations.

What is claimed is:

1. A reactor which comprises a first housing, partition means disposed within said first housing to define therein an inner flow passage and an outer flow passage disposed in laterally surrounding relation to said inner flow passage and flow connected therewith, means defining an inlet in said first housing to accommodate the introduction therein of a liquid sample and a gas to be reacted with said sample, a packing material disposed in said inner flow passage to define therein an inlet plenum zone communicating with said inlet, and a packing material disposed in said outer flow passage, means defining an outlet in said first housing communicating with said outer flow passage, means operable to heat the packing material in said inner and outer flow passages to a temperature at which the sample is vaporized in said inlet plenum zone and the sample reacts with said gas while flowing therewith through said inner and outer passages in contact with the packing material, the gaseous and vapor reaction products of said sample and gas exiting the first housing through said outlet, said first housing having a cylindrical shell outer wall and a pair of plates connected each to a respective end of said outer wall, and said partition means including a cylindrical tubular inner wall extending between said plates and disposed in generally coaxial relation to said outer wall to define a cylindrical inner flow passage and an annular outer flow passage, the outlet of said first housing being through said outer wall, a second housing defining an outlet plenum chamber and connected at one end to said outer wall of the first housing for support thereby and communicating with said outlet thereof to receive said gaseous and vapor reaction products to cool same, said second housing having an outlet for the exits of such cooled reaction products as are not condensed to liquid, and separate outlet for drainage of such reaction products as are condensed to liquid, said second housing being inclined in a downward direction to facilitate drainage of such liquid.

2. A reactor according to claim 1 wherein said packing material in said inner flow passage is a plurality of balls disposed in contact with one another to establish voids accommodating fluid flow through said passage, said balls being located generally in the lower half of said inner flow passage to define an inlet plenum zone in the upper half thereof.

3. A reactor according to claim 1 wherein said packing material in said outer flow passage is a plurality of balls disposed in contact with one another to establish voids accommodating fluid flow through said passage.

* * * * *